US00PP15972P2

(12) United States Plant Patent
Hofmann et al.

(10) Patent No.: US PP15,972 P2
(45) Date of Patent: Sep. 20, 2005

(54) ***NEMESIA* PLANT NAMED 'N006-9BLAU'**

(50) Latin Name: ***Nemesia* hybrid**
Varietal Denomination: N006-9BLAU

(75) Inventors: Silvia Hofmann, Mainz (DE); Susanne Herdegen, Dexheim (DE); Hendrik Theobald, Heidesheim (DE)

(73) Assignee: InnovaPlant GmbH & Co. K.G., Gensingen (DE)

( * ) Notice: Subject to any disclaimer, the term of this patent is extended or adjusted under 35 U.S.C. 154(b) by 49 days.

(21) Appl. No.: 10/960,684

(22) Filed: Oct. 6, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,014 P2 * 7/2001 Hubbard ..... Plt./263
PP13,229 P2 * 11/2002 Hammett ..... Plt./263
2004/0128726 P1 * 7/2004 Trees ..... Plt./263

OTHER PUBLICATIONS

UPOV ROM GTITM Computer Database, GTI Jouve Retrieval Software 2004/05 Citation for 'N006–9BLAU'.*

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Nemesia* plant named 'N006-9BLAU', characterized by its upright plant habit; freely branching habit; early flowering habit; and numerous purple-colored flowers that are fragrant.

1 Drawing Sheet

Botanical designation: *Nemesia* hybrid.
Variety denomination: 'N006-9BLAU'.

BACKGROUND OF THE INVENTION

The present invention relates to a new and distinct cultivar of *Nemesia* plant, botanically known as *Nemesia* hybrid and referred to by the name 'N006-9BLAU'.

The new *Nemesia* is a product of a planned breeding program conducted by the Inventors in Gensingen, Germany. The objective of the program is to create new compact and early-flowering *Nemesia* cultivars with numerous flowers, unique flower colors and fragrance.

The new *Nemesia* originated from a cross-pollination made by the Inventors of a proprietary *Nemesia* hybrid selection identified as code N98Sä3tetra2, not patented, as the female, or seed, parent with the *Nemesia* hybrid cultivar Hubbird, disclosed in U.S. Plant Pat. No. 12,014, as the male, or pollen, parent during the summer of 1999. The cultivar N006-9BLAU was discovered and selected by the Inventors as a flowering plant within the progeny of the stated cross-pollination in a controlled environment in Gensingen, Germany during the summer of 1999.

Asexual reproduction of the new *Nemesia* by terminal cuttings in a controlled environment in Gensingen, Germany since 1999, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'N006-9BLAU' and distinguish 'N006-9BLAU' as a new and distinct cultivar:

1. Upright plant habit.
2. Freely branching habit.
3. Early flowering habit.
4. Numerous purple-colored flowers that are fragrant.

Plants of the new *Nemesia* differ primarily from plants of the female parent selection in the following characteristics:

1. Plants of the new *Nemesia* flower earlier than plants of the female parent selection.
2. Plants of the new *Nemesia* have larger flowers than plants of the female parent selection.
3. Plants of the new *Nemesia* are more freely flowering than plants of the female parent selection.

Plants of the new *Nemesia* differ primarily from plants of the male parent, the cultivar Hubbird, in the following characteristics:

1. Flower color of plants of the new *Nemesia* is more intense than flower color of plants of the cultivar Hubbird.
2. Flowers of plants of the new *Nemesia* are more fragrant than flowers of plants of the cultivar Hubbird.

Plants of the new *Nemesia* can be compared to plants of the cultivar Melanie, not patented. In side-by-side comparisons conducted in Gensingen, Germany, plants of the new *Nemesia* differed from plants of the cultivar Melanie in the following characteristics:

1. Plants of the new *Nemesia* were more vigorous than plants of the cultivar Melanie.
2. Plants of the new *Nemesia* had larger flowers than plants of the cultivar Melanie.
3. Flower color of plants of the new *Nemesia* was more intense than flower color of plants of the cultivar Melanie.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia.*

The photograph at the top of the sheet comprises a side perspective view of a typical plant of 'N006-9BLAU' grown in a container.

The photograph at the bottom of the sheet comprises a close-up view of typical flowers of 'N006-9BLAU'.

DETAILED BOTANICAL DESCRIPTION

The aforementioned photographs and following observations and averaged measurements describe plants grown in Bonsall, Calif., in an outdoor nursery during the spring with day temperatures ranging from 18 to 35° C. and night temperatures ranging from 7 to 18° C. After rooting, plants were grown for four weeks in 15-cm containers with three plants per container. Color references are made to The Royal Horticultural Society Colour Chart, 1995 Edition, except where general terms of ordinary dictionary significance are used.

Botanical classification: *Nemesia* hybrid cultivar N006-9BLAU.

Parentage:

*Female parent.*—Proprietary *Nemesia* hybrid selection identified as code N98Sã3tetra2, not patented.

*Male parent.*—*Nemesia* hybrid cultivar Hubbird, disclosed in U.S. Plant Pat. No. 12,014.

Propagation:

*Type.*—By vegetative cuttings.

*Time to initiate roots.*—About 10 to 14 days at 20° C.

*Time to develop roots.*—About two to three weeks at 20° C.

*Root description.*—Fine; freely branching; white in color.

Plant description:

*General appearance.*—Upright plant habit; inverted triangle. Freely branching, typically about six primary lateral branches each with about four six secondary lateral branches. Numerous purple-colored zygomorphic flowers. Vigorous growth habit.

*Plant height.*—About 27 cm.

*Plant diameter or spread.*—About 22 cm.

*Lateral branches.*—Appearance: Square in cross-section with longitudinal ridges. Length: About 25 cm. Diameter: About 4 mm. Internode length: About 3.5 to 4.5 cm. Strength: Strong. Texture: Glabrous. Color: 144A.

*Foliage description.*—Arrangement: Opposite, simple. Shape: Elliptic to lanceolate. Apex: Broadly acute. Base: Attenuate. Length: About 4.5 cm. Width: About 2.5 cm. Margin: Serrate. Texture, upper and lower surfaces: Glabrous. Venation pattern: Pinnate, arcuate. Petiole length: About 4 mm. Petiole diameter: About 5 mm. Color: Developing leaves, upper surface: 146A. Developing leaves, lower surface: 147B. Fully expanded leaves, upper surface: 147A. Fully expanded leaves, lower surface: 147B. Venation, upper and lower surfaces: 147B. Petiole: 144A.

Flowering description:

*Arrangement/appearance.*—Zygomorphic solitary flowers arranged on terminal racemes; flowering acropetally towards apex. Flowers bilabiate with nectar spur. Flowers face outward. Flowers last about four to five days on the plant. Flowers not persistent.

*Natural flowering season.*—Natural flowering season is spring to fall; flowering continuous during this period.

*Quantity of flowers.*—Freely flowering with about 17 to 20 flowers and flower buds per raceme at one time.

*Fragrance.*—Floral-like.

*Inflorescence length.*—About 11 cm.

*Inflorescence diameter.*—About 4 cm.

*Flower diameter.*—About 1.8 cm by 1.8 cm.

*Flower depth, including nectar spur.*—About 2.3 cm.

*Flower buds.*—Shape: Ovoid with spur. Length including spur: About 1 cm. Diameter: About 7 mm. Color: 76B.

*Petals.*—Arrangement/shape: Five petals. Four upper petals are fused at base to form an upright lobed and arched banner lip; lower petal modified into a larger lip with nectar spur and convex oval protuberance which serves as pollinator nectar guide and landing platform. Apex: Rounded. Margin: Entire. Length: Upper lip petals: About 8 mm. Lower lip petal: About 1 cm. Width: Upper lip petals: About 4 to 8 mm. Lower lip petal: About 1.3 cm. Texture, upper and lower surfaces: Smooth, velvety. Color: When opening, upper surface: 85A. When opening, lower surface: 76D. Fully opened, upper surface: 86B; color becoming closer to 92A with development. Fully opened, lower surface: 85A. Nectar guide: 4A. Nectar spur: Close to 85A.

*Sepals.*—Quantity: Five-parted, star-shaped calyx. Shape: Elliptic. Apex: Acute. Base: Fused. Margin: Entire. Length: About 4 mm. Diameter: About 2 mm. Texture, upper and lower surfaces: Pubescent. Color, upper and lower surfaces: 147B.

*Peduncle.*—Length: About 5.5 cm. Diameter: About 2 mm. Strength: Strong. Angle: Upright to 45° from the stem. Color: 144A.

*Pedicel.*—Length: About 8 mm. Diameter: About 1 mm. Strength: Slender, but holds flowers outward. Angle: About 45° from the stem. Color: 144B.

*Androecium.*—Stamen number: Four per flower. Anther shape: Oval. Anther length: Less than 1 mm. Anther color: 14A. Amount of pollen: Scarce. Pollen color: 14A.

*Gynoecium.*—Pistil number: One per flower. Pistil length: About 3 mm. Style length: About 1.5 mm. Style color: 157C. Stigma shape: Rounded. Stigma color: 145C. Ovary color: 145A.

*Seed/fruit.*—Seed and fruit production has not been observed on plants of the new *Nemesia.*

Disease/pest resistance: Plants of the new *Nemesia* have not been observed to be resistant to pathogens or pests common to *Nemesias.*

Temperature tolerance: Plants of the new *Nemesia* have been observed to be tolerant to temperatures ranging from 2° to 35° C.

It is claimed:

1. A new and distinct cultivar of *Nemesia* plant named 'N006-9BLAU', as illustrated and described.

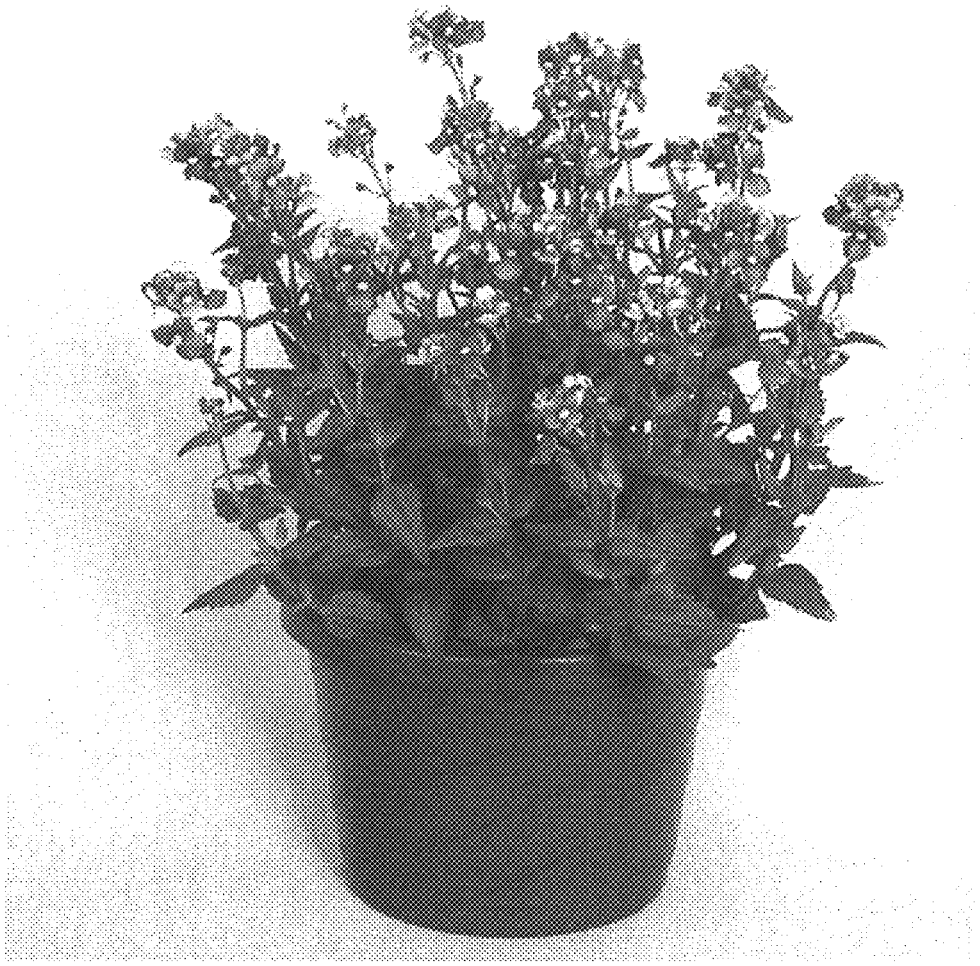
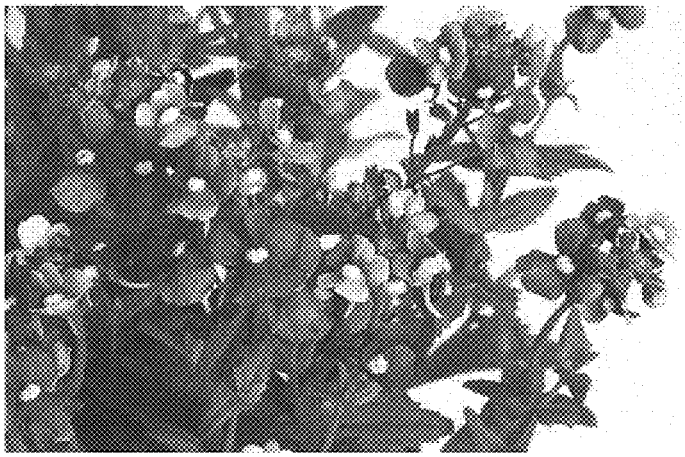

* * * * *